United States Patent
Macevicz

(10) Patent No.: US 7,682,791 B2
(45) Date of Patent: Mar. 23, 2010

(54) METHOD OF GENERATING NESTED SETS OF DOUBLE STRANDED DNA CIRCLES

(76) Inventor: Stephen C. Macevicz, 21890 Rucker Dr., Cupertino, CA (US) 95014

(*) Notice: Subject to any disclaimer, the term of this patent is extended or adjusted under 35 U.S.C. 154(b) by 144 days.

(21) Appl. No.: 11/923,655

(22) Filed: Oct. 25, 2007

(65) Prior Publication Data

US 2008/0102466 A1    May 1, 2008

Related U.S. Application Data

(60) Provisional application No. 60/886,323, filed on Jan. 24, 2007, provisional application No. 60/864,405, filed on Nov. 5, 2006, provisional application No. 60/863,387, filed on Oct. 29, 2006.

(51) Int. Cl.
*C12Q 1/68* (2006.01)
(52) U.S. Cl. .................. 435/6; 435/91.1; 435/91.2
(58) Field of Classification Search .................. None
See application file for complete search history.

(56) References Cited

U.S. PATENT DOCUMENTS

| | | | | |
|---|---|---|---|---|
| 4,293,652 | A | 10/1981 | Cohen | 435/172 |
| 5,593,826 | A * | 1/1997 | Fung et al. | 435/6 |
| 5,773,238 | A | 6/1998 | Shukla | 435/41 |
| 6,489,103 | B1 | 12/2002 | Griffiths | 435/6 |
| 2004/0005594 | A1 | 1/2004 | Holliger | 435/6 |
| 2005/0064460 | A1 | 3/2005 | Holliger | 435/6 |
| 2005/0260570 | A1 | 11/2005 | Mao | 435/6 |
| 2006/0024681 | A1 * | 2/2006 | Smith et al. | 435/6 |
| 2006/0068390 | A1 | 3/2006 | Tillett | 435/6 |
| 2007/0065823 | A1 | 3/2007 | Dressman | 435/6 |

OTHER PUBLICATIONS

Ghadessy et al, "Directed evolution of polymerase function by compartmentalized self-replication," Proc. Natl. Acad. Sci., 98: 4552-4557 (2001).
Griffiths et al, "Miniaturising the laboratory in emulsion droplets," Trends in Biotechnology, 24: 395-402 (2006).
Li et al, "BEAMing up for detection and quantification of rare sequence variants," Nature Methods, 3: 95-97 (2006)(including supplemental materials).
Musyanovych et al, "Miniemulsion droplets as single molecule nanoreactors for polymerase chain reaction," Biomacromolecules, 6: 1824-1828 (2005).
Shendure et al, "Accurate multiplex polony sequencing of an evolved bacterial genome," Science, 309: 1728-1732 (2005)(including supplemental material).
Shore et al, "DNA flexibility studied by covalent closure of short fragments into circles," Proc. Natl. Acad. Sci., 78: 4833-4837 (1981).
Wolters et al, "Construction of a 42 base pair double stranded DNA microcircle," Nucleic Acids Research, 17: 5163-5172 (1989).

* cited by examiner

*Primary Examiner*—Heather G Calamita
(74) *Attorney, Agent, or Firm*—Stephen C. Macevicz

(57) ABSTRACT

The invention provides a method of generating nested sets of double stranded DNA (dsDNA) circles that may be used as size ladders in nucleic acid separations and as templates in DNA sequencing operations. In one aspect, the invention provides methods for generating nested sets of double stranded DNA circles in a self-sustaining enzymatic reaction comprising the activities of at least one endonuclease, at least one single stranded exonuclease, and at least one ligase. In another embodiment, such nested sets are generated from linear dsDNA fragments having ligatable terminators that are self-ligated to form corresponding dsDNA circles.

10 Claims, 8 Drawing Sheets

METHOD OF GENERATING NESTED SETS OF DOUBLE STRANDED DNA CIRCLES

This application claims priority under the following U.S. provisional applications: U.S. application No. 60/863,387 filed Oct. 29, 2006, U.S. application No. 60/864,405 filed Nov. 5, 2006, and U.S. application No. 60/886,323 filed Jan. 24, 2007, each of which is hereby incorporated by reference in its entirety.

BACKGROUND

It is often useful for processes in molecular biology, such as size determination, sequence determination, or the like, to generate sets of related polynucleotides that differ in length by regular amounts, Sanger et al, Proc. Natl. Acad. Sci., 74: 5463-5467 (1977); Brenner, U.S. Pat. No. 5,552,278; Hyman, U.S. Pat. No. 5,840,757; Hartley, U.S. Pat. No. 6,680,378; Hu et al, U.S. Pat. No. 6,924,098; Carlson et al, U.S. Pat. No. 5,316,908; and the like.

SUMMARY OF THE INVENTION

The invention provides a method of generating nested sets of double stranded DNA (dsDNA) circles that may be used as size ladders in nucleic acid separations and as templates in DNA sequencing operations. In one aspect, the invention provides methods for generating nested sets of double stranded DNA circles of various types. In one embodiment of this aspect, such nested sets are generated in a self-sustaining enzymatic reaction comprising the activities of at least one endonuclease, at least one single stranded exonuclease, and at least one ligase. In another embodiment of this aspect, Such nested sets are generated from linear dsDNA fragments having ligatable terminators that are self-ligated to form corresponding dsDNA circles. In another aspect, the invention provides compositions of nested sets of double stranded DNA circles for use in analytical techniques including size determinations of nucleic acid fragments by separation. DNA sequence determination, and the like.

DETAILED DESCRIPTION OF THE INVENTION

Figure 1A:
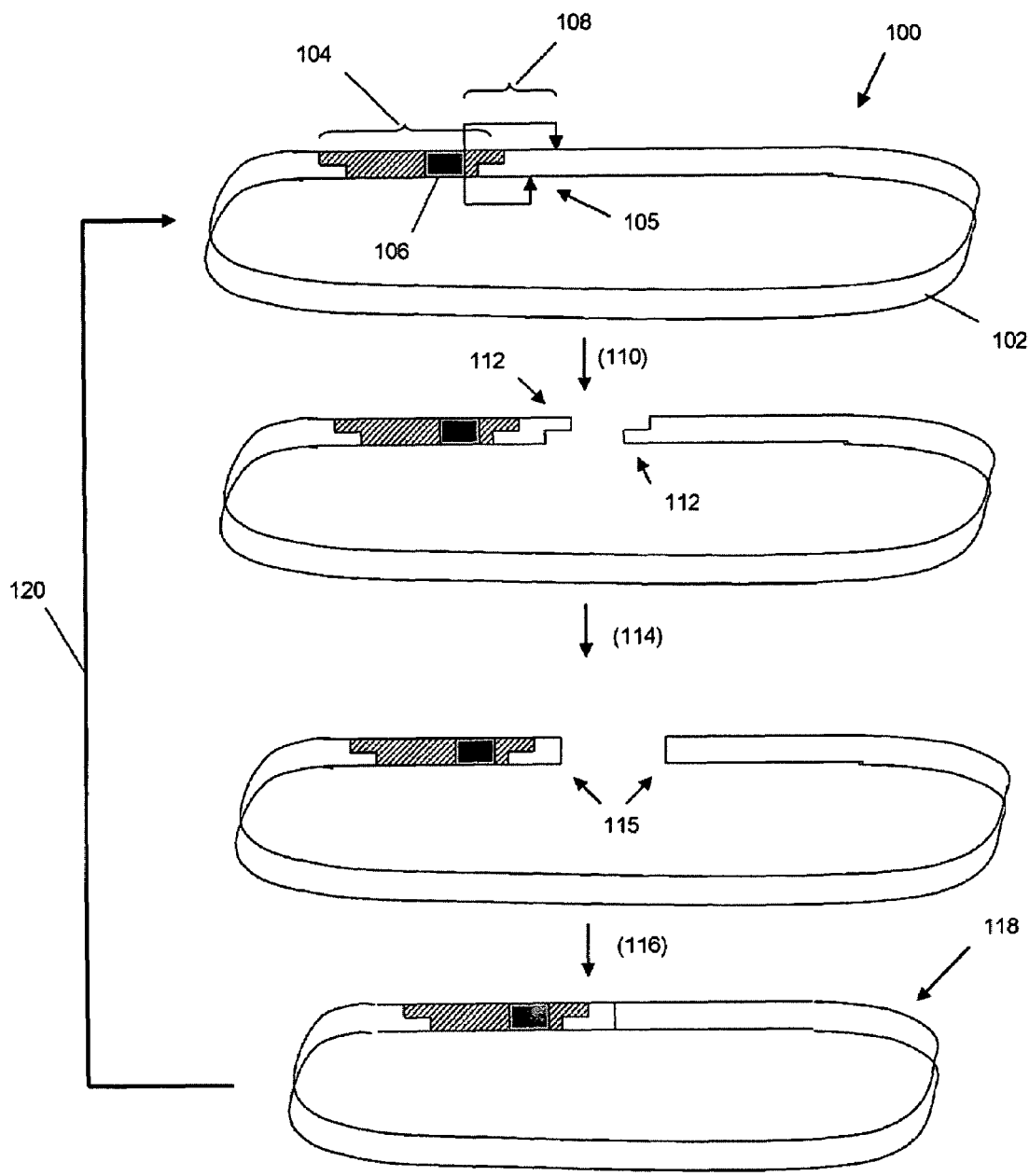
FIGS. 1A-1B illustrate a cyclical reaction of the invention for producing a nested set of dsDNA circles.

The practice of the present invention may employ, unless otherwise indicated, conventional techniques and descriptions of organic chemistry, molecular biology (including recombinant techniques), cell biology, biochemistry, and immunology, which are within the skill of the art. Such conventional techniques include, but are not limited to, vector construction, microbial host transformation, selection and application of genetic markers, manipulation of large polynucleotide fragments, preparation of synthetic polynucleotides, application of recombination systems, nucleic acid sequencing and analysis, polymer array synthesis, hybridization, ligation, detection of hybridization using labels, and the like. Specific illustrations of suitable techniques can be had by reference to the example herein below. However, other equivalent conventional procedures can, of course, also be used. Such conventional techniques and descriptions can be found in standard laboratory manuals such as *Genome Analysis: A Laboratory Manual Series* (Vols. I-IV), *Using Antibodies: A Laboratory Manual, Cells: A Laboratory Manual, PCR Primer: A Laboratory Manual*, and *Molecular Cloning: A Laboratory Manual* (all from Cold Spring Harbor Laboratory Press), Stryer, L. (1995) *Biochemistry* (4th Ed.) Freeman, New York, Gait, "*Oligonucleotide Synthesis: A Practical Approach*" 1984, IRL Press, London, Nelson and Cox (2000), *Lehninger, Principles of Biochemistry* $3^{rd}$ Ed., W. H. Freeman Pub., New York, N.Y. and Berg et al. (2002) *Biochemistry*, $5^{th}$ Ed., W. H. Freeman Pub., New York, N.Y., all of which are herein incorporated in their entirety by reference for all purposes.

The invention provides methods of making nested sets of double stranded DNA circles and methods of using such sets in the determination of the sequence of DNA fragments and as chromatographic or electrophoretic size standards, particularly after linearization. Compositions of the invention may have a variety of embodiments. In one embodiment, compositions of the invention comprises a nested set of double stranded DNA circles, wherein each double stranded DNA circle in such set comprises a DNA fragment and at least one adaptor having a recognition site for an endonuclease having a cleavage site separate from its recognition site, the recognition site being oriented such that the cleavage site is within the DNA fragment a predetermined distance, the nested set comprising a plurality of such double stranded DNA circles such that each member of the plurality has a DNA fragment truncated by an integral number of segments, each segment having a length equivalent to the predetermined distance. As used herein, the term "predetermined distance" means a length of DNA. In one form, the predetermined distance is a length of DNA between an end of an adaptor. e.g. (104), and the cleavage site of an endonuclease that has a recognition site within the adaptor, e.g. (106). Thus, in this form, the predetermined distance depends on the position of the recognition site, e.g. (106) within the adaptor, e.g. (104), and the "reach" (108)(i.e. the distance of the cleavage site from the recognition site) of the endonuclease. In one aspect, a composition has a plurality of at least three double stranded DNA circles with different numbers of truncations. In another aspect, a predetermined distance is selected that results in truncations in the range of from one to four nucleotides, inclusive. Compositions of the invention may vary widely as to their relative amounts of truncation products of DNA fragments. Preferably, a majority of the truncated DNA fragments within a nested set are truncated by between zero and ten segments. In another preferred embodiment, a majority of the truncated DNA fragments within a nested set are truncated by between zero and six segments. Usually, the length of an adaptor together with a DNA fragment forming a double stranded DNA circle is long enough to permit bending so that the ends of such a conjugate can be juxtaposed for ligation. Typically, such conjugates are in a range of a few tens of basepairs, e.g. 40, to a few thousand basepairs, e.g. 5000.

Circle Generation by Self-Sustained Reactions

Figure 1B:
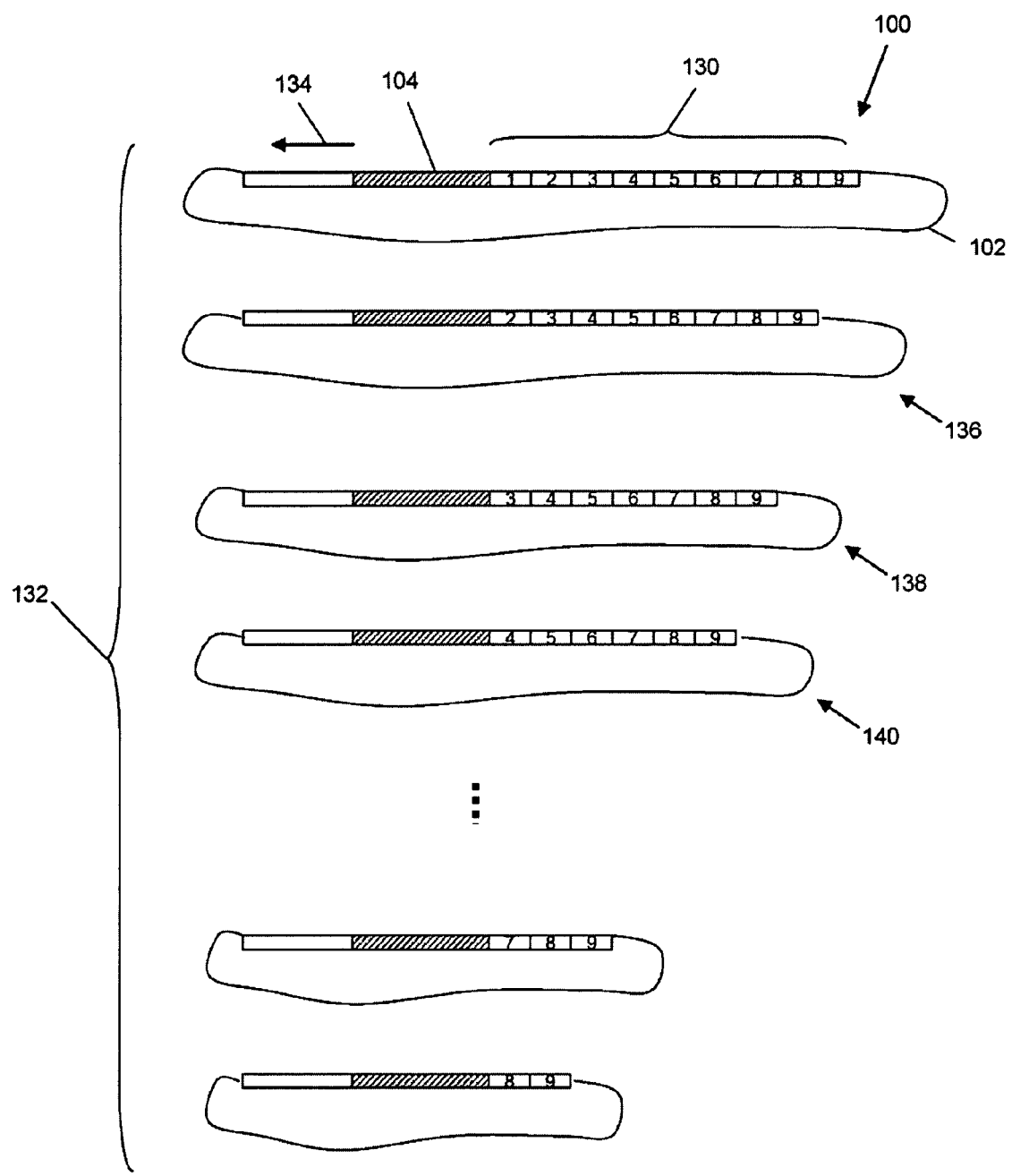

In one aspect, the invention provides a cyclical self-sustaining reaction based on the presence of at least three enzymatic activities of cleavage, polishing, and ligation in the same reaction mixture. As used herein, "polishing" refers to an enzymatic activity that modifies an end of a double stranded DNA having an overhang to remove such overhang to produce a blunt, or flush, end; that is, an end with no overhanging, or unpaired, terminal nucleotides. Preferably, such flush ends are ligatable, such as, by having a free 5' phosphate. One or more DNA fragments are circularized in the presence of an adaptor so that dsDNA circles are formed, such as taught by Shendure et al (2005), Science, 309: 1728-1732; Smith et al, U.S. patent publication 2006/0024681; or the like, which are incorporated herein by reference. The adaptor contains a type IIs restriction site oriented so that the cleavage site of its cognate endonuclease is in the interior of the DNA fragment. The one or more DNA circles are combined with a ligase, a single stranded exonuclease, and a type IIs restriction endonuclease that recognizes the restriction site of the adaptor, where upon a cyclical reaction takes place, as illustrated in FIG. 1A. dsDNA circle (100) comprises DNA fragment (102) and adaptor (104), and adaptor (104) contains a restriction site for a type IIs restriction endonuclease whose cleavage site is located (105) within DNA fragment (102), wherein the "distance" of cleavage site (105) within DNA fragment (102) depends on the position of recognition site (106) within adaptor (104) and reach (108) of the restriction endonuclease, as mentioned above. Cleavage (110) by the type IIs restriction endonuclease generates overhanging strands (112), which may be either 5' overhanging strands or 3' overhanging strands. In one aspect, the overhanging strands are 3' strands and the polishing enzyme is a DNA polymerase having 3'→5' exonuclease activity. In one embodiment, such DNA polymerase is T4 DNA polymerase or DNA polymerase I (E. coli). In another aspect, the overhanging stands are 5' strands and the polishing enzyme is Mung bean endonuclease. Action (114) by the polishing enzyme produces blunt ends (115) on the open dsDNA circles, which are ligated (116) together to form shortened dsDNA circle (118). Upon ligation, shortened dsDNA circle becomes an available substrate for cleavage by the type IIs restriction endonuclease, thereby reentering (120) the reaction cycle. As the reaction progresses a population of dsDNA circles of different sizes is produced for each different DNA fragment in the reaction mixture. That is, the reaction may be implemented with a single starting dsDNA circle (a single-plex reaction) or with a starting population of different dsDNA circles (a multiplex reaction). For each starting dsDNA circle, a nest set of dsDNA circles is generated. As used herein, "nested set" means a set of nucleic acids that have identical nucleotide sequences at one end (or region) and at the other end (or in another portion) the members members differ by one or more truncations, where each truncation is of the same length. Typically, the truncations have a size in the range of from 1 to 4 nucleotides. FIG. 1B illustrates a nested set (132) of dsDNA circles produced by a cyclical reaction of the invention. Each dsDNA circle is the sane to the left (or counter-clockwise) (134) of adaptor segment (104). To the right of adaptor (104) DNA fragment (102) has been shortened by incremental amounts, or truncations, which are designated as numbered rectangles in the figure for convenience. Top-most dsDNA circle (100) has not undergone any shortening, so it is shown to contain segments 1 through 9. Depending on the reaction conditions selected, the relative numbers in each size class may vary. Other members of the nested set are missing segments 1 (136), segments 1 and 2 (138), segments 1, 2, and 3 (140), and so on. Region (134) to the left of adaptor (104) may be used to identify members of a nested set in a multiplexed reaction mixture. Also, an oligonucleotide tag may be inserted (or included in the adaptor sequence) in order to identify members of the same nested set in a multiplex reaction. Unique oligonucleotide tags may be attached directly when dsDNA circles are prepared or indirectly in a "labeling by sampling" procedure, e.g. as disclosed by Brenner et al, U.S. Pat. No. 5,846,719, which is incorporated by reference. The distribution of the different size classes may be varied by varying the various enzymatic activities in conventional ways, such as by enzyme selection, variation of relative and absolute enzyme concentrations, addition of crowding agents, employing water-in-oil emulsion systems, and the like.

There is abundant guidance for selecting reaction conditions for conducting the above enzymatic reactions. In particular, guidance for DNA circularization reactions is disclosed in the following references: Cohen, U.S. Pat. No. 4,293,652; Collins et al, Proc. Natl. Acad. Sci., 81: 6812-6816 (1984); Weissman et al, U.S. Pat. No. 5,118,604; Ng et al, Nature Methods, 2: 105-111 (2005); Ng et al. Nucleic Acids Research, 34: e84 (2006); Smith et al. U.S. patent publication 2006/0024681; and the like, which are incorporated by reference. Water-in-oil emulsion reaction conditions are of interest to promote blunt-end ligation, e.g. as disclosed by Margulies et al, Nature, 437: 376-380 (2005); Shendure et al (2005), Science, 309: 1728-1732; Berka et al, U.S. patent publication 2005/0079510; Church et al, PCT publication WO 2005/082098; Nobile et al, U.S. patent publication 2005/0227264; Griffiths et al, U.S. Pat. No. 6,489,103; Tillett et al, PCT publication WO 03/106678; Kojima et al, Nucleic Acids Research, 33 (17): e150 (2005); Dressman et al, Proc. Natl. Acad. Sci., 100: 8817-8822 (2003); Mitra et al, Anal. Biochem., 320: 55-65 (2003); Musyanovych et al, Biomacromolecules, 6: 1824-1828 (2005); Li et al, Nature Methods, 3: 95-97 (2000); and the like, which are incorporated herein by reference. Use of molecular crowding reagents in enzymatic reactions are disclosed in the following references: Takahashi et al, J. Biochem, 100: 123-131 (1986); Zimmerman et al, Proc. Natl. Acad. Sci., 80: 5852-5856 (1983); Zimmerman et al, Annu. Rev. Biophys. Biomol. Struct., 22: 27-65 (1993); Schnell et al, Prog. Biophys. Mol. Biol., 85: 235-260 (2004); Minton, Meth. Enzymol., 295: 127-149 (1998); Chebotareva et al, Biochemistry (Moscow), 69: 1239-1251 (2004); and the like, which are incorporated by reference. DNA fragments used to construct double stranded DNA circles are produced by conventional fragmentation techniques, such as chemical fragmentation, enzymatic fragmentation, or mechanical fragmentation. In one aspect, such DNA fragments are restriction fragments.

Exemplary type IIs restriction endonucleases that produce 3' overhanging strands include AcuI, BciVI, BmrI, BpmI, BpuEI, BseMII, BseRI, BsgI, BtsI, EciI, Eco57MI, HphI, MboII, MmeI, MnlI, and the like. Exemplary type IIs restriction endonucleases that produce 5' overhanging strands include BbsI, BbvI, BceAI, BfuAI, BsaI, BsmAI, EarI, FokI, SapI, and the like.

Exemplary reaction conditions. A lest DNA fragment is produced by ligating a synthesized 20 basepair adaptor into EcoRI-HindIII digested pUC19 DNA, after which a suitable host is transformed, grown, and the modified pUC19 is isolated. The adaptor sequence is selected so that it contains a BpmI site oriented so that its cleavage site is downstream of the HindIII site of the pUC19. The modified pUC19 is digested with DrdI, the smaller fragment containing the adaptor is isolated and circularized. In a 20 μL volume, the following reagents are combined: 0.5 μM circularized DNA fragments, 1 μL T4 ligase (400,000 U/mL), 1 mM ATP, 25 μg/mL BSA, 50 mM NaCl, 10 mM Tris-HCl (pH 7.9 @ 25° C.), 10 mM $MgCl_2$, 1 mM dithiotlireitol, 200 units of BpmI, 20 units T4 DNA polymerase. After incubation for 2-4 hours at 25° C., the reaction is stopped by addition of EDTA (to 10 mM) and/or heating and the nested set of dsDNA circles is harvested. Optionally, single stranded exonuclease may be added to the reaction after stopping by heating to reduce the background of non-circularized DNA.

Figure 2A:
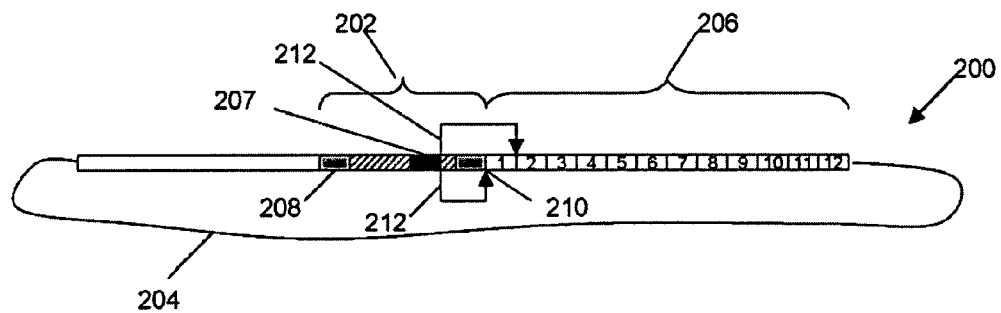
FIGS. 2A-2C illustrate an application of the invention to high-throughput sequencing of nucleic acids.
Figure 2B:
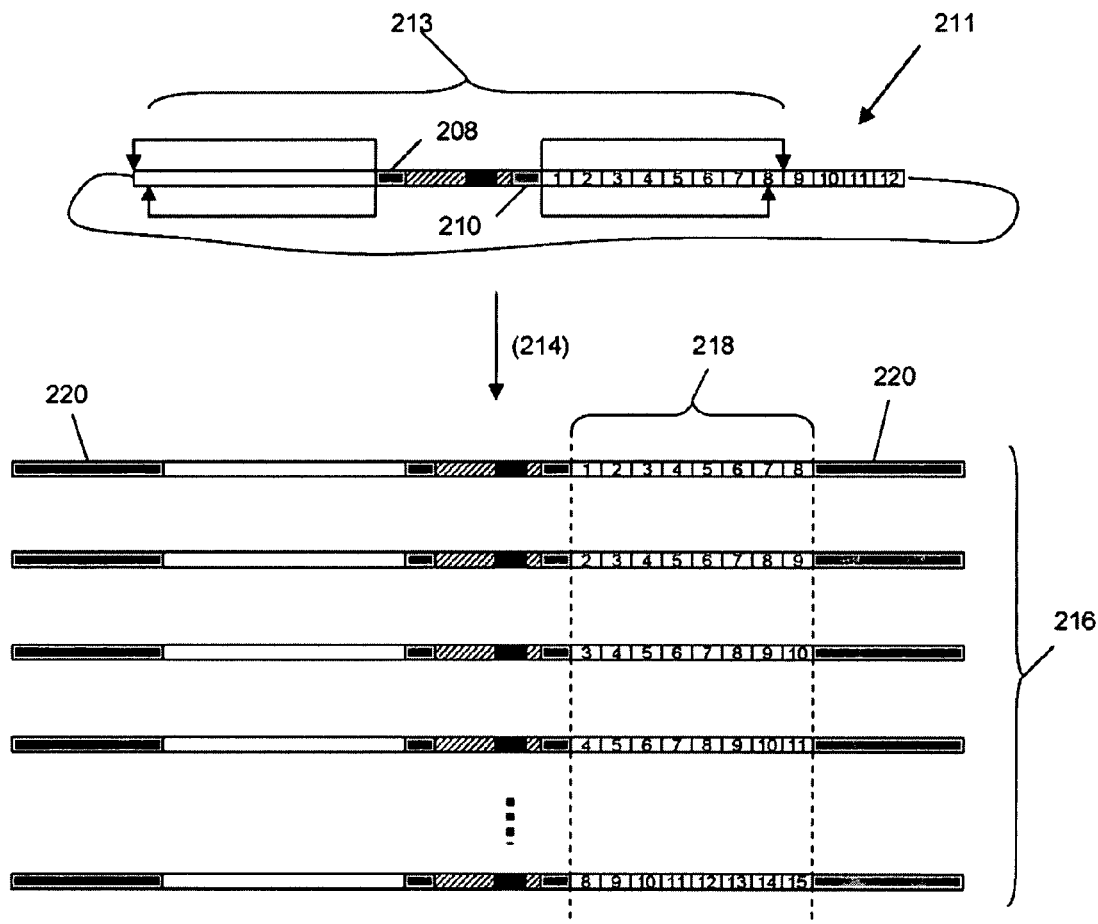
Figure 2C:
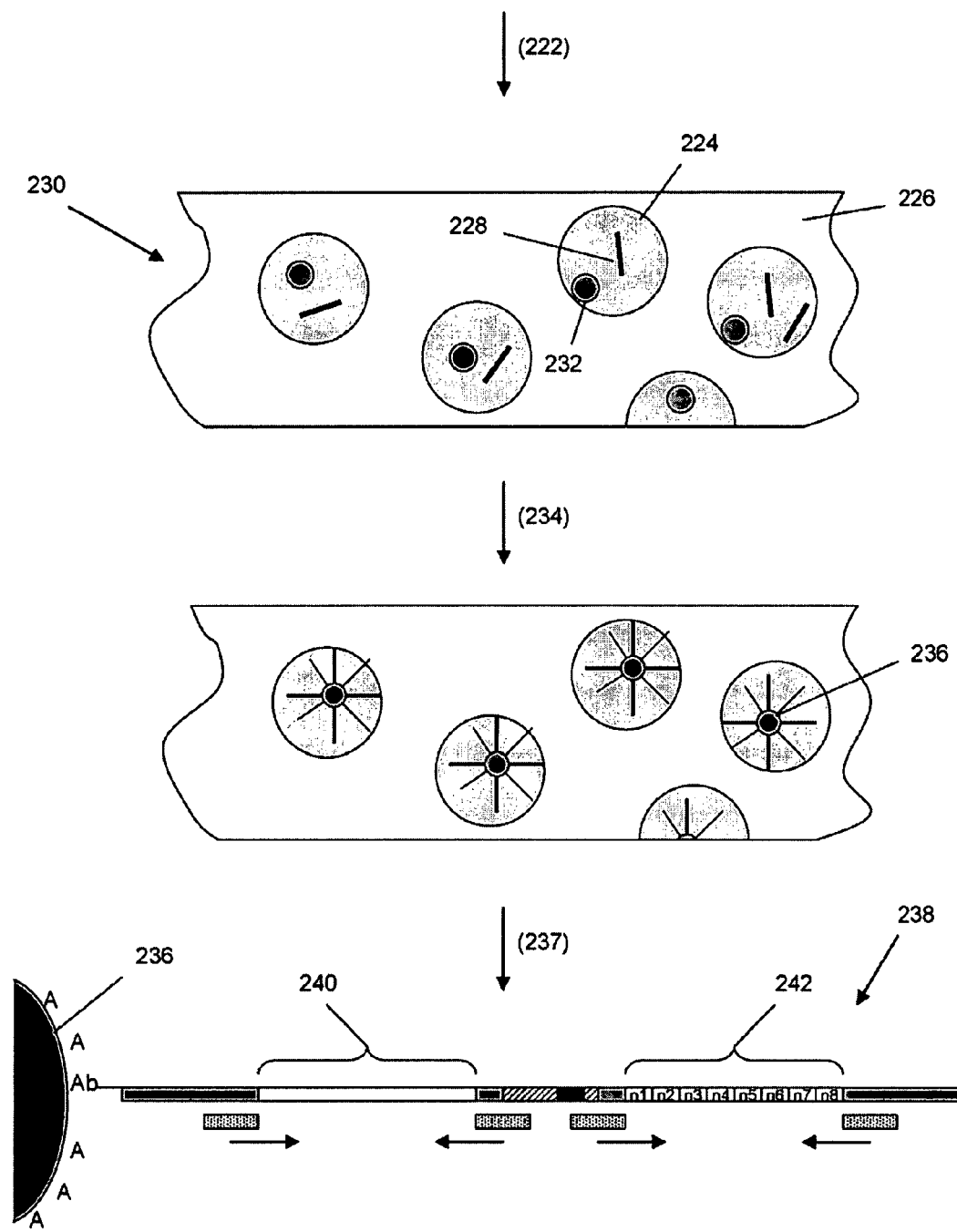

In one aspect, an adaptor used to construct a starting population of dsDNA circles may include primer binding sites sandwiching a restriction site, e.g. having an 8-mer recognition site to minimize spurious cleavage of the DNA fragments. After nested sets of dsDNA circles are formed in a reaction of the invention, the resulting circles may be linearized and amplified in an emulsion PCR reaction as taught by Shendure et al (2005, cited above), after which the bead-bound amplicons may be analyzed by ligation-based sequencing methods or by sequencing by synthesis sequencing methods. Sequences determined from one primer binding site of the amplicons will be the same, whereas sequences determined from the other primer will depend on number of deletions the parent dsDNA circle went through in the reaction to form nested sets. The latter sequences of members of the same nested set are correlated with one another by their common sequence as determined from their other primer binding site. When the sequencing approach provides sufficiently long sequence read lengths, then the sequences of each nested set may be assembled by overlapping subsequences. These concepts are illustrated in FIGS. 2A-2B. Double stranded DNA circle (200) comprises adaptor (202) and DNA fragment (204). One end (206) of DNA fragment (204) is sub-divided into unit of sequence that are deleted by operation of the method of the invention, which in part depends on a first type IIs restriction endonuclease that recognizes restriction site (207). The first restriction endonuclease cleaves the dsDNA circle at sites in DNA fragment (204) removed predetermined distances (212) from recognition site (207). Adaptor (202) further comprises second type IIs restriction endonuclease recognition site (208) and third type IIs restriction endonuclease recognition site (210) oriented so that both have cleavage sites within DNA fragment (204) on opposite sides of adaptor (202). As shown in FIG. 2B, after generation of a nested set of dsDNA circles (211) (only one shown), the population is treated with second (208) and third (210) type IIs restriction endonucleases to generate a population of fragments (213) comprising adaptor (202) sandwiched in between end segments of DNA fragments (204), which are referred to herein as "mate-pairs" of fragments (204). End adaptors (220) are ligated (214) to the ends of fragments (213) to generate population (216) of adaptored mate-pairs. For each fragment (204), there is a family, or nested set, of mate-pairs (218), each having a different number of deletions from the end adjacent to adaptor (202). These families may be analyzed by high-throughputs sequencing methodologies that make use of mate-pair structures, such as those disclosed by Shendure et al (cited above), Margulies et al (cited above), and the like. For example, fragments of population (216) may be amplified and attached as clonal populations to beads using emulsion PCR, as illustrated in FIG. 2C. Fragments (216) are mixed (222) with PCR reagents and beads with primers attached, and then with an oil to form an emulsion (230) that contains aqueous micelles (224) in an oil (226). Conditions are selected so that a significant fraction of micelles (224) contain a single bead (232) and a single fragment (228). PCR is then implemented (234) to generated a population of micelles containing single beads (236) with clonal populations of fragments attached, which populations are amplicons of fragments (216). The sequences (238) of the mate-pairs (240 and 242) on such beads may analyzed (237), for example, as taught by Shendure et al (cited above), where cycles of primer annealing, probe ligation, base identification, and washing, are carried out at the four ends of male-pairs (240 and 242).

Figure 3A:
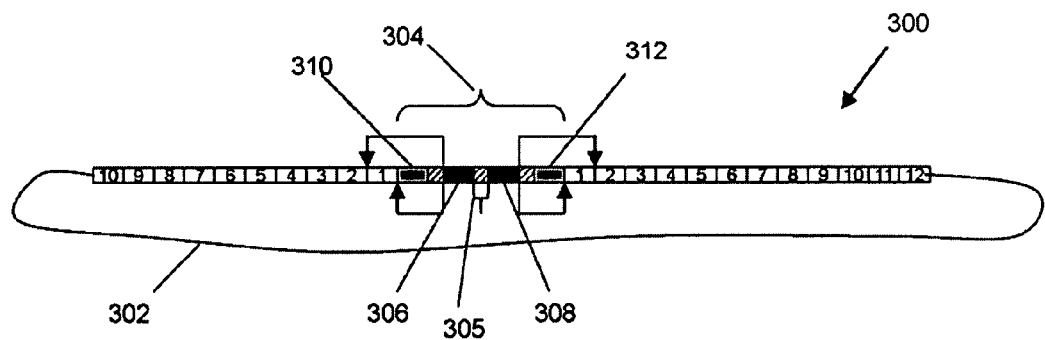
FIGS. 3A-3B illustrate a method of generating a double nested set double stranded DNA circles.
Figure 3B:
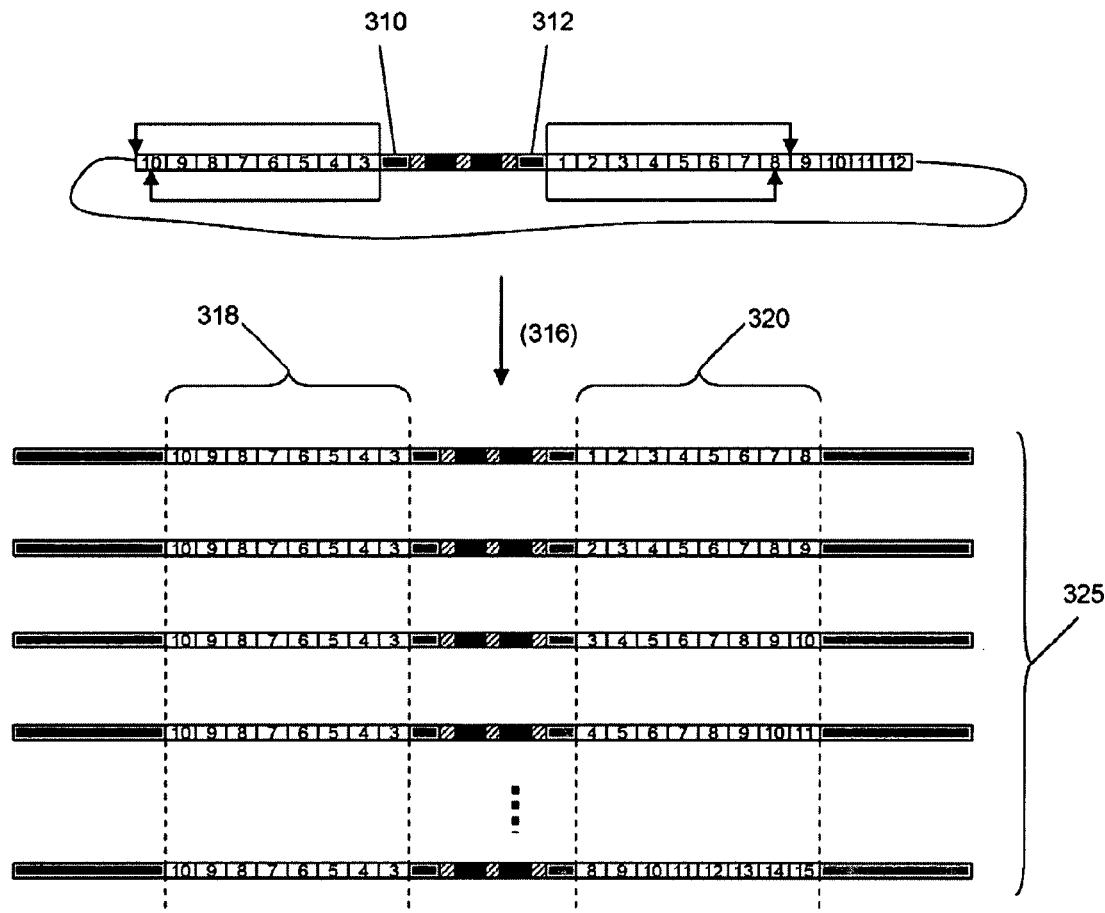

In one aspect of the invention, double nested sets of dsDNA circles may be generated, as shown in FIGS. 3A and 3B. As above, starting material is dsDNA circle (300) comprising DNA fragment(s) (302) and adaptor (304). Again, sequences at the ends or DNA fragment (302) have been sub-divided into subunits to show where deletions occur in the generation of nested sets. In this aspect, adaptor (304) contains two different type IIs restriction endonucleases (306) and (308) for generating cleavages at opposite ends of adaptor (304) in two successive rounds of the self-sustaining three-enzyme reaction of the invention. That is, the procedure described above in connection with FIG. 2A is applied successively initially using first type IIs restriction enzyme (310) in the self-sustaining reaction, and then using second type IIs restriction endonuclease (312) in the self-sustaining reaction to produce a double nested set of dsDNA circles. As above, adaptor (304) may also include type IIs restriction endonucleases (310) and (312) for generating mate-pairs from the population of double nested ds DNA products. Region (305) of adaptor (304) may contain additional elements such as oligonucleotide lags, additional primer binding sites, or the like. After the formation or mate-pairs and cleavage with restriction endonucleases (310) and (312), the excised mate-pairs have adaptors ligated (316) to their ends to form population (325) of double nested dsDNA fragments, whose mate-pairs may be analyzed as described above. It is noted that in population (325), only one left deletion segment is shown in (318); that is, the deletion segment comprising subunits 10 through 3. This deletion segment is paired with ever) possible right deletion segment making up the right hand member of the mate-pairs; that is (as shown under (320)), right deletion segments having subunits: 1 through 8, 2 through 9, 3 through 10, and so on.

Figure 4:
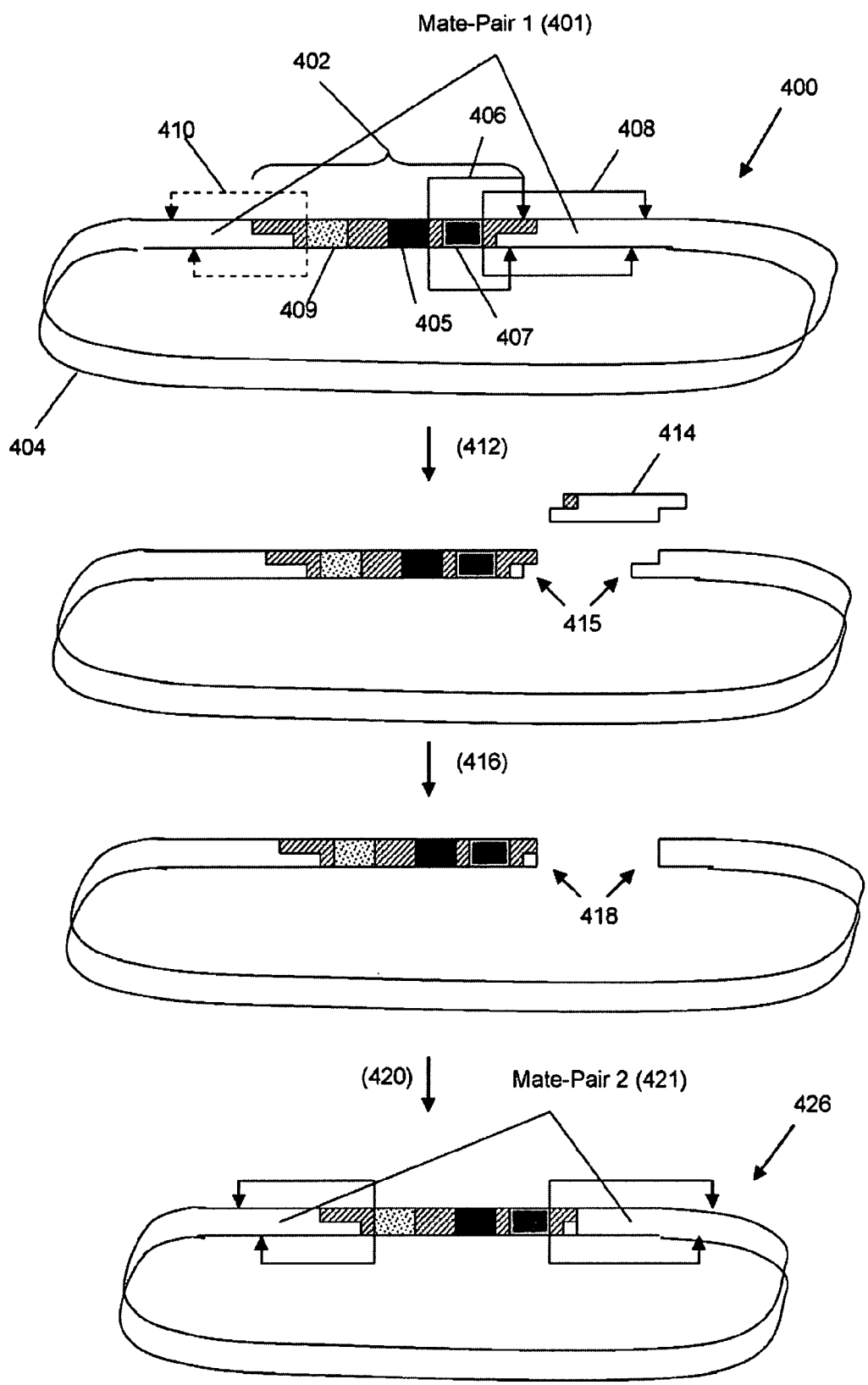
FIG. 4 illustrates the generation of populations of mixed mate-pairs using the principle of the present invention.

In still another application of the present invention, sets of mate-pairs may be produced that contain families of related mate-pairs that are made by one or more deletions in accordance with the invention. In this embodiment, a self-sustaining reaction is not established so that a well-defined number of deletions are made in a step-wise manner. As illustrated in FIG. 4, dsDNA circle (400) comprises DNA fragment (404) and adaptor (402), which in turn comprises three type IIs restriction endonucleases (405), (407), and (409), which have cleave sites spaced as shown by (406), (408), and (410), respectively. Cleavage sites (407) and (409) correspond to different type IIs enzymes so that the enzymes may be used separately to make cleavage either to the right of adaptor (402) or to the left of adaptor (402). In accordance with one embodiment of this aspect, dsDNA circle is divided into two portions. A first portion may be processed as taught by Shendure et al (cited above) and others to produce a first mate-pair (401). A second portion may be cleaved (412) by enzymes recognizing sites (405) and (407) to excise fragment (414) from dsDNA circle (400), after which ends (415) are polished (416) to form blunt ends (418). Blunt ends (418) are ligated (420) for form dsDNA circle (426), which may be processed as above to form second mate-pairs (421). The two sets of mate-pairs may be analyzed together or separately and their respective sequence pairs are related by the common sequence of one of member of the pairs. As above, in another embodiment, adaptor (402) may include an oligonucleotide tags by which to relate the sequences of related mate-pairs. Also as above, controlled deletion may be made from both ends of adaptor (402) so that families of four related mate-pairs are produced, or additional cleavages and removals of segments may be implemented to further increase mate-pair family sizes.

Circle Generation by Multiplex Extensions

Figure 5A:
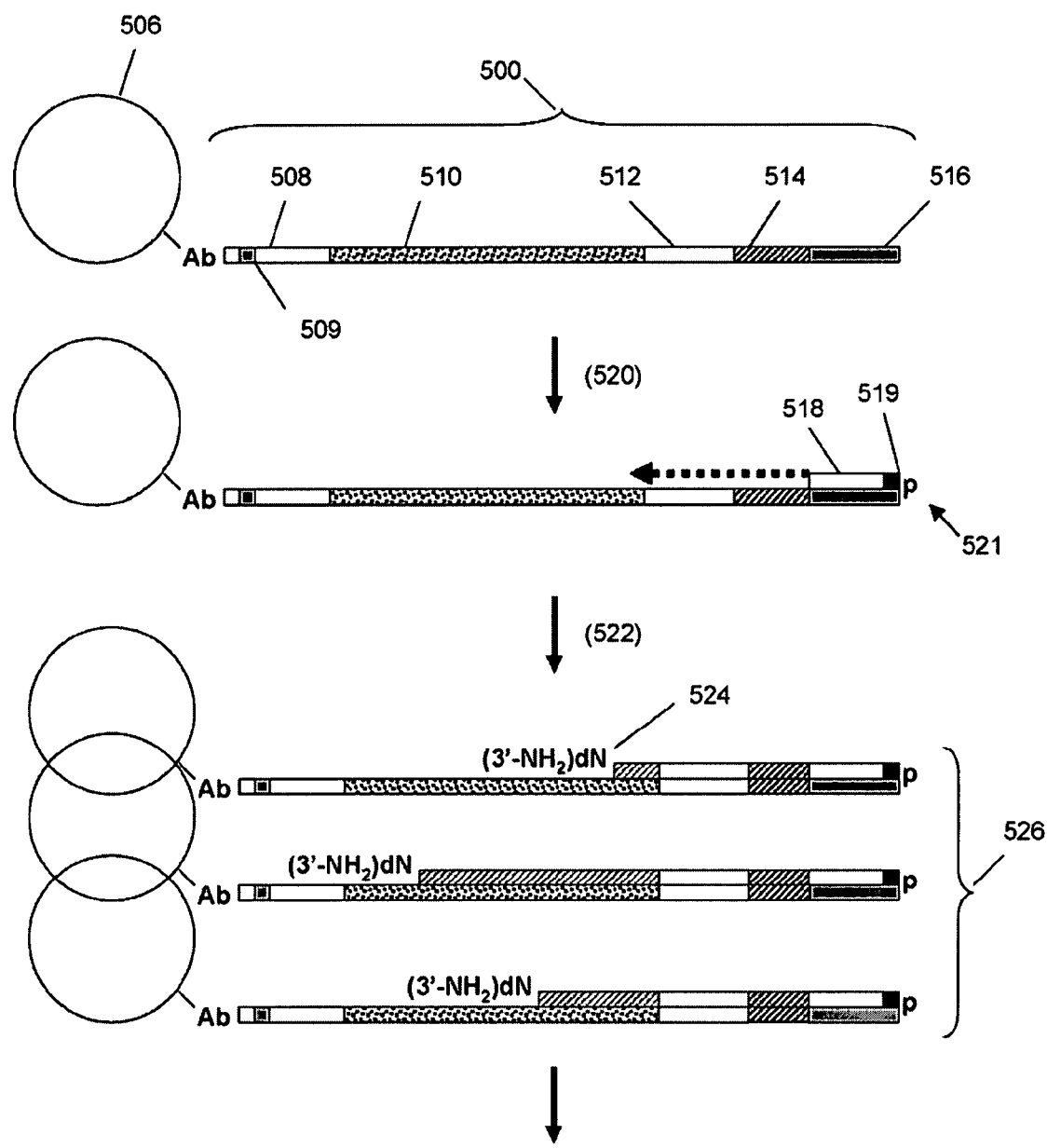
FIGS. 5A-5B illustrate a non-cyclical reaction of the invention for producing a nested set of dsDNA circles.
Figure 5B:
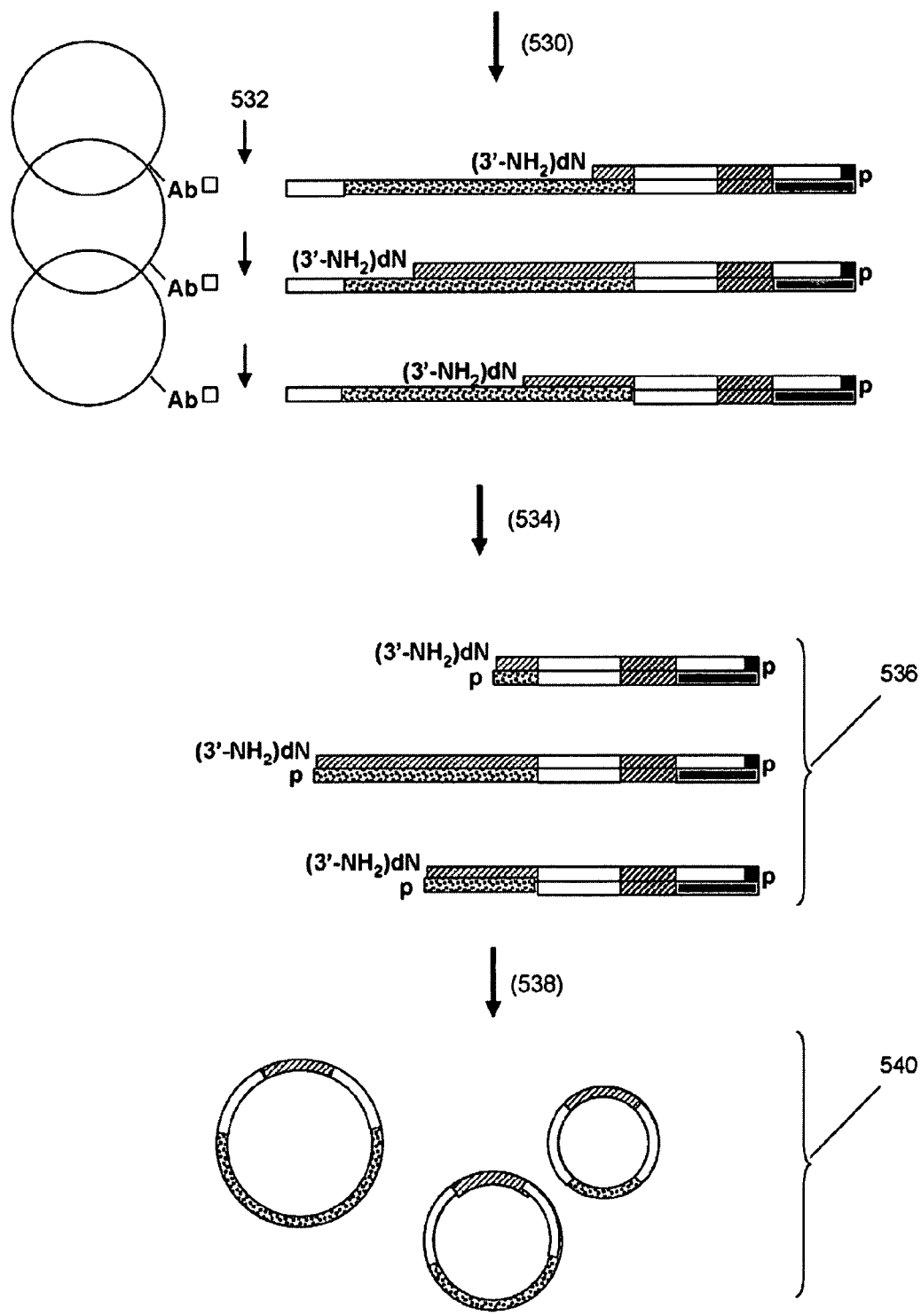

In another aspect the method of the invention is implemented by generating a nested set of dsDNA fragments in a non-cyclical, or non-self-sustaining, reaction followed by auto-ligation, as is illustrated in FIGS. 5A-5B. Each target polynucleotide is amplified, either alone or together with other target polynucleotides in a multiplex reaction, to produce an amplicon having a single strand (500) comprising the following elements: At one end, there is capture moiety (502), such as a biotin, for binding to a reciprocal moiety, such as avidin or streptavidin, which, in turn, is attached to solid support (506). Capture moiety (502) can be attached to target polynucleotide (510) in a polymerase chain reaction (PCR), as described more fully below, which creates primer binding site (508) in single strand (500). In one aspect, a primer is employed in such PCR that contains deoxyuridine residue (509) that, after incorporation into (500), is used later to cleave single strands (500) from solid support (506) in a conventional uracil-DNA glycosylase reaction. At the end of target polynucleotide (510) opposite of primer binding site (508) in sequence is primer binding site (512), oligonucleotide tag (514), and primer binding site (516). After amplicons containing single strands (500) are produced, they are capture by solid phase supports (506). To such captured strands are annealed (520) primers (518) to site (516), after which they are extended (522) in a conventional DNA polymerase reaction in the presence of ligatable chain terminators (524), such as 3'-aminodeoxynucleoside triphosphates, e.g. as disclosed in Gryaznov and Fung, U.S. Pat. No. 5,593,826, which is incorporated herein by reference. In such a reaction containing ligatable chain terminators for each of the four natural nucleotides, extension products (526) are formed that terminate with an A, C, G, and T, respectively, and a nested set of fragments are produced wherein each member fragment of the set differs in length by one nucleotide from other members of the set. Preferably, primer (518) has 5'-phosphate group (521), so that the strand may participate in a later self-ligation reaction, and contains nuclease-resistant linkage at its 5' end to protect it from degradation in later steps using 5'-nucleases.

Captured extension products (526) are released from solid supports (506) by treating (530) them with a uracil-DNA glycosylase and/or heat, thereby cleaving single strands (500) within (532) primer binding site (508) proximal to solid phase support (506). The released strands are then treated with a single stranded 5'-exonuclease, such as Mung Bean exonuclease, RecJ$_1$ exonuclease, or the like, to produce nested set of blunt-ended dsDNA fragments (536), which are then circularized (538) in a conventional circularization reaction to produce nested set of dsDNA circles (540). Guidance for carrying out such circularization reaction is disclosed in the following references, which are incorporated by reference: Smith et al, U.S. patent publication 2006/0024681; Ulanovsky et al, Proc. Natl. Acad. Sci., 83: 862-66 (1986); Shore et al. Proc. Natl. Acad. Sci., 78: 4833-4837 (1981); Vaudin et al, Nucleic Acids Research, 23: 670-674 (1995); Wolters et al, Nucleic Acids Research, 17: 5163-5172 (1989); Shendure et al, Science, 309: 1728-1732 (including Supplemental Materials); Wang and Davidson, J. Mol. Biol., 19: 469-482 (1966); and the like.

DEFINITIONS

Terms and symbols of nucleic acid chemistry, biochemistry, genetics, and molecular biology used herein follow those of standard treatises and texts in the field, e.g. Kornberg and Baker, DNA Replication, Second Edition (W.H. Freeman, New York, 1992); Lehninger, Biochemistry, Second Edition (Worth Publishers, New York, 1975); Strachan and Read, Human Molecular Genetics, Second Edition (Wiley-Liss, New York, 1999); Eckstein, editor, Oligonucleotides and Analogs: A Practical Approach (Oxford University Press, New York, 1991); Gail, editor, Oligonucleotide Synthesis: A Practical Approach (IRL Press, Oxford, 1984); and the like.

"Amplicon" means the product of a polynucleotide amplification reaction. That is, it is a population of polynucleotides, usually double stranded, that are replicated from one or more starting sequences. The one or more starting sequences may be one or more copies of the same sequence, or it may be a mixture of different sequences. Amplicons may be produced by a variety of amplification reactions whose products are multiple replicates of one or more target nucleic acids. Generally, amplification reactions producing amplicons are "template-driven" in that base pairing of reactants, either nucleotides or oligonucleotides, have complements in a template polynucleotide that are required for the creation of reaction products. In one aspect, template-driven reactions are primer extensions with a nucleic acid polymerase or oligonucleotide ligations with a nucleic acid ligase. Such reactions include, but are not limited to, polymerase chain reactions (PCRs), linear polymerase reactions, nucleic acid sequence-based amplification (NASBAs), rolling circle amplifications, and the like, disclosed in the following references that are incorporated herein by reference: Mullis et al, U.S. Pat. Nos. 4,683, 195; 4,965,188; 4,683,202; 4,800,159 (PCR). Gelfand et al, U.S. Pat. No. 5,210,015 (real-time PCR with "taqman" probes); Wittwer et al, U.S. Pat. No. 6,174,670; Kacian et al, U.S. Pat. No. 5,399,491 ("NASBA"); Lizardi, U.S. Pat. No. 5,854,033; Aono et al, Japanese patent publ. JP 4-262799 (rolling circle amplification); and the like. In one aspect, amplicons of the invention are produced by PCRs. An amplification reaction may be a "real-time" amplification if a detection chemistry is available that permits a reaction product to be measured as the amplification reaction progresses, e.g. "real-time PCR" described below, or "real-time NASBA" as described in Leone et al, Nucleic Acids Research, 26: 2150-2155 (1998), and like references. As used herein, the term "amplifying" means performing an amplification reaction. A "reaction mixture" means a solution containing all the necessary reactants for performing a reaction, which may include, but not be limited to, buffering agents to maintain pH at a selected level during a reaction, salt, co-factors, scavengers, and the like.

"Complementary or substantially complementary" refers to the hybridization or base pairing or the formation of a duplex between nucleotides or nucleic acids, such as, for instance, between the two strands of a double stranded DNA molecule or between an oligonucleotide primer and a primer binding site on a single stranded nucleic acid. Complementary nucleotides are, generally, A and T (or A and U), or C and G. Two single stranded RNA or DNA molecules are said to be substantially complementary when the nucleotides of one strand, optimally aligned and compared and with appropriate nucleotide insertions or deletions, pair with at least about 80% of the nucleotides of the other strand, usually at least about 90% to 95%, and more preferably from about 98 to 100%. Alternatively, substantial complementarity exists when an RNA or DNA strand will hybridize wider selective hybridization conditions to its complement. Typically, selective hybridization will occur when there is at least about 65% complementary over a stretch of at least 14 to 25 nucleotides, preferably at least about 75%, more preferably at least about 90% complementary. See, M. Kanehisa Nucleic Acids Res. 12:203 (1984), incorporated herein by reference.

"Duplex" means at least two oligonucleotides and/or polynucleotides that are fully or partially complementary undergo Watson-Crick type base pairing among all or most of their nucleotides so that a stable complex is formed. The terms "annealing" and "hybridization" are used interchangeably to mean the formation of a stable duplex. "Perfectly matched" will reference to a duplex means that the poly- or oligonucleotide strands making up the duplex form a double stranded structure with one another such that every nucleotide in each strand undergoes Watson-Crick basepairing with a nucleotide in the outer strand. The term "duplex" comprehends the pairing of nucleoside analogs, such as deoxyinosine, nucleosides with 2-aminopurine bases, PNAs, and the like, that may be employed. A "mismatch" in a duplex between two oligonucleotides or polynucleotides means that a pair of nucleotides in the duplex fails to undergo Watson-Crick bonding.

"Hybridization" refers to the process in which two single-stranded polynucleotides bind non-covalently to form a stable double-stranded polynucleotide. The term "hybridization" may also refer to triple-stranded hybridization. The resulting (usually) double-stranded polynucleotide is a "hybrid" or "duplex." "Hybridization conditions" will typically include salt concentrations of less than about 1M, more usually less than about 500 mM and less than about 200 mM. A "hybridization buffer" is a buffered salt solution such as 5×SSPE, or the like. Hybridization temperatures can be as low as 5° C., but are typically greater than 22° C., more typically greater than about 30° C., and preferably in excess of about 37° C. Hybridizations are usually performed under stringent conditions, i.e. conditions under which a probe will hybridize to its target subsequence. Stringent conditions are sequence-dependent and are different in different circumstances. Longer fragments may require higher hybridization temperatures for specific hybridization. As other factors may affect the stringency of hybridization, including base composition and length of the complementary strands, presence of organic solvents and extent of base mismatching, the combination of parameters is more important than the absolute measure of any one alone. Generally, stringent conditions are selected to be about 5° C. lower than the $T_m$ for the specific sequence at s defined ionic strength and pH. Exemplary stringent conditions include salt concentration of at least 0.01 M to no more than 1 M Na ion concentration (or other salts) at a pH 7.0 to 8.3 and a temperature of at least 25° C. For example, conditions of 5×SSPE (750 mM NaCl, 50 mM NaPhosphate, 5 mM EDTA, pH 7.4) and a temperature of 25-30° C. are suitable for allele-specific probe hybridizations. For stringent conditions, see for example, Sambrook, Fritsche and Maniatis. "Molecular Cloning A laboratory Manual" $2^{nd}$ Ed. Cold Spring Harbor Press (1989) and Anderson "Nucleic Acid Hybridization" $1^{st}$ Ed., BIOS Scientific Publishers Limited (1999), which are hereby incorporated by reference in its entirety for all purposes above. "Hybridizing specifically to" or "specifically hybridizing to" or like expressions refer to the binding, duplexing, or hybridizing of a molecule substantially to or only to a particular nucleotide sequence or sequences under stringent conditions when that sequence is present in a complex mixture (e.g., total cellular) DNA or RNA.

"Ligation" means to form a covalent bond or linkage between the termini of two or more nucleic acids, e.g. oligonucleotides and/or polynucleotides, in a template-driven reaction. The nature of the bond or linkage may vary widely and the ligation may be carried out enzymatically or chemically. As used herein, ligations are usually carried out enzymatically to form a phosphodiester linkage between a 5' carbon of a terminal nucleotide of one oligonucleotide with 3' carbon of another oligonucleotide. A variety of template-driven ligation reactions are described in the following references, which are incorporated by reference: Whitely et al, U.S. Pat. No. 4,883,750; Letsinger et al, U.S. Pat. No. 5,476,930; Fung et al, U.S. Pat. No. 5,593,826; Kool, U.S. Pat. No. 5,426,180; Landegren et al, U.S. Pat. No. 5,871,921; Xu and Kool, Nucleic Acids Research, 27: 875-881 (1999); Higgins et al, Methods in Enzymology, 68: 50-71 (1979); Engler et al, The Enzymes, 15: 3-29 (1982); and Namsaraev, U.S. patent publication 2004/0110213. Enzymatic ligation usually takes place in a ligase buffer, which is a buffered salt solution containing any required divalent cations, cofactors, and the like, for the particular ligase employed.

"Mismatch" means a base pair between any two of the bases A, T (or U for RNA), G, and C other than the Watson-Crick base pairs G-C and A-T. The eight possible mismatches are A-A, T-T, G-G, C-C, T-G, C-A, T-C, and A-G.

"Nucleoside" as used herein includes the natural nucleosides, including 2'-deoxy and 2'-hydroxyl forms, e.g. as described in Kornberg and Baker, DNA Replication, 2nd Ed. (Freeman, San Francisco, 1992). "Analogs" in reference to nucleosides includes synthetic nucleosides having modified base moieties and/or modified sugar moieties, e.g. described by Scheit, Nucleotide Analogs (John Wiley, New York, 1980); Uhlman and Peyman, Chemical Reviews, 90: 543-584 (1990), or the like, with the proviso that they are capable of specific hybridization. Such analogs include synthetic nucleosides designed to enhance binding properties, reduce complexity, increase specificity, and the like. Polynucleotides comprising analogs with enhanced hybridization or nuclease resistance properties are described in Uhlman and Peyman (cited above); Crooke et al, Exp. Opin. Ther. Patents, 6: 855-870 (1996); Mesmaeker et al, Current Opinion in Structural Biology, 5: 343-355 (1995); and the like. Exemplary types of polynucleotides that are capable of enhancing duplex stability include oligonucleotide N3'→P5' phosphoramidates (referred to herein as "amidates"), peptide nucleic acids (referred to herein as "PNAs"), oligo-2'-O-alkylribonucleotides, polynucleotides containing C-5 propynylpyrimidines, locked nucleic acids (LNAs), and like compounds. Such oligonucleotides are either available commercially or may be synthesized using methods described in the literature.

"Oligonucleotide tag" means an oligonucleotide that is attached to a polynucleotide and is used to identify and/or track the polynucleotide in a reaction. Usually, an oligonucleotide tag is attached to the 3'- or 5'-end of a polynucleotide to form a linear conjugate, sometime referred to herein as a "tagged polynucleotide," or equivalently, an "oligonucleotide tag-polynucleotide conjugate," or "tag-polynucleotide conjugate," or similar term. Lengths of oligonucleotide tags can vary widely, and the selection of a particular length depend on several factors including, without limitation, whether the oligonucleotide tags are employed primarily in hybridization reactions or primarily in enzymatic reactions, whether they are labeled, whether such labeling is direct or indirect, the number of distinguishable oligonucleotide tags required, and the like. Exemplary oligonucleotide tags are disclosed in the following references: Brenner et al, U.S. Pat. No. 5,846,719; Mao et al (cited above); Fan et al, International patent publication WO 2000/058516; Morris et al, U.S. Pat. No. 6,458,530; Morris et al, U.S. patent publication 2003/0104436; Church et al, European patent publication 0 303 459; Huang et al, U.S. Pat. No. 6,709,816; which references are incorporated herein by reference.

"Polymerase chain reaction," or "PCR," means a reaction for the in vitro amplification of specific DNA sequences by the simultaneous primer extension of complementary, strands of DNA. In other words, PCR is a reaction for making multiple copies or replicates of a target nucleic acid flanked by primer binding sites, such reaction comprising one or more repetitions of the following steps: (i) denaturing the target nucleic acid, (ii) annealing primers to the primer binding sites, and (iii) extending the primers by a nucleic acid polymerase in the presence of nucleoside triphosphates. Usually, the reaction is cycled through different temperatures optimized for each step in a thermal cycler instrument. Particular temperatures, durations at each step, and rates of change between steps depend on many factors well-known to those of ordinary skill in the art, e.g. exemplified by the references: McPherson et al, editors, PCR: A Practical Approach and PCR2: A Practical Approach (IRL Press, Oxford, 1991 and 1995, respectively). For example, in a conventional PCR using Taq DNA polymerase, a double stranded target nucleic acid may be denatured at a temperature >90° C., primers annealed at a temperature in the range 50-75° C., and primers extended at a temperature in the range 72-78° C. The term "PCR" encompasses derivative forms of the reaction, including but not limited to, RT-PCR, real-time PCR, nested PCR, quantitative PCR, multiplexed PCR, and the like. Reaction volumes range from a few hundred nanoliters, e.g. 200 nL, to a few hundred μL, e.g. 200 μL.

"Polynucleotide" or "oligonucleotide" are used interchangeably and each mean a linear polymer of nucleotide monomers. As used herein, the terms may also refer to double stranded forms. Monomers making up polynucleotides and oligonucleotides are capable of specifically binding to a natural polynucleotide by way of a regular pattern of monomer-to-monomer interactions, such as Watson-Crick type of base pairing, base stacking, Hoogsteen or reverse Hoogsteen types of base pairing, or the like, to form duplex or triplex forms. Such monomers and their internucleosidic linkages may be naturally occurring or may be analogs thereof, e.g. naturally occurring or non-naturally occurring analogs. Non-naturally occurring analogs may include PNAs, phosphorothioate internucleosidic linkages, bases containing linking groups permitting the attachment of labels, such as fluorophores, or haptens, and the like. Whenever the use of an oligonucleotide or polynucleotide requires enzymatic processing, such as extension by a polymerase, ligation by a ligase, or the like, one of ordinary skill would understand that oligonucleotides or polynucleotides in those instances would not contain certain analogs of internucleosidic linkages, sugar moities, or bases at any or some positions, when such analogs are incompatible with enzymatic reactions. Polynucleotides typically range in size from a few monomeric units, e.g. 5-40, when they are usually referred to as "oligonucleotides." to several thousand monomeric units. Whenever a polynucleotide or oligonucleotide is represented by a sequence of letters (upper or lower case), such as "ATGCCTG," it will be understood that the nucleotides are in 5'→3' order from left to right and that "A" denotes deoxyadenosine, "C" denotes deoxycytidine, "G" denotes deoxyguanosine, and "T" denotes thymidine, "I" denotes deoxyinosine, "U" denotes uridine, unless otherwise indicated or obvious from context. Unless otherwise noted the terminology and atom numbering conventions will follow those disclosed in Strachan and Read, Human Molecular Genetics 2 (Wiley-Liss, New York, 1999). Usually polynucleotides comprise the four natural nucleosides (e.g. deoxyadenosine, deoxycytidine, deoxyguanosine, deoxythymidine for DNA or their ribose counterparts for RNA) linked by phosphodiester linkages; however, they may also comprise non-natural nucleotide analogs, e.g. including modified bases, sugars, or internucleosidic linkages. It is clear to those skilled in the art that where an enzyme has specific oligonucleotide or polynucleotide substrate requirements for activity, e.g. single stranded DNA, RNA/DNA duplex, or the like, then selection of appropriate composition for the oligonucleotide or polynucleotide substrates is well within the knowledge of one of ordinary skill, especially with guidance from treatises, such as Sambrook et al, Molecular Cloning, Second Edition (Cold Spring Harbor Laboratory, New York, 1989), and like references.

"Primer" means an oligonucleotide, either natural or synthetic, that is capable, upon forming a duplex with a polynucleotide template, of acting as a point of initiation of nucleic acid synthesis and being extended from its 3' end along the template so that an extended duplex is formed. The sequence of nucleotides added during the extension process are determined by the sequence of the template polynucleotide. Usually primers are extended by a DNA polymerase. Primers usually have a length in the range of from 9 to 40 nucleotides, or in some embodiments, from 14 to 36 nucleotides.

"Readout" means a parameter, or parameters, which are measured and/or detected that can be converted to a number or value. In some contexts, readout may refer to an actual numerical representation of such collected or recorded data. For example, a readout of fluorescent intensity signals from a microarray is the position and fluorescence intensity of a signal being generated at each hybridization site of the microarray; thus, such a readout may be registered or stored in various ways, for example, as an image of the microarray, as a table of numbers, or the like.

"Sequence determination" in reference to a target polynucleotide means determination of information relating to the sequence of nucleotides in such target polynucleotide. Such information may include the identification or determination of partial as well as full sequence information of the target polynucleotide. The sequence information may be determined with varying degrees of statistical reliability or confidence. In one aspect, the term includes the determination of the identity, ordering, and locations of one, two, three, or four types of nucleotides within a target polynucleotide. For example, in some embodiments sequence determination may be effected by identifying the ordering and locations of a single type of nucleotide, e.g. cytosines, within a target polynucleotide. For example, in the sequence "CATCGC . . . " sequence information may be obtained that is represented as a binary code, e.g. "100101 . . . " for "C-(not C)-(not C)-C-(not C) . . . " and the like. In another aspect, sequence information means the identity and ordering of a plurality of contiguous nucleotides in a target polynucleotide. In still another aspect, sequence information includes the identity and ordering of a plurality of nucleotides within a target polynucleotide that are not contiguous. In another aspect, the identities and ordering of a plurality of nucleotides may be known, but spacing between adjacent nucleotides may not be known, or only known to within a range of possible values.

"Specific" or "specificity" in reference to the binding of one molecule to another molecule, such as a labeled target sequence for a probe, means the recognition, contact, and formation of a stable complex between the two molecules, together with substantially less recognition, contact, or complex formation of that molecule with other molecules. In one aspect, "specific" in reference to the binding of a first molecule to a second molecule means that to the extent the first molecule recognizes and forms a complex with another molecules in a reaction or sample, it forms the largest number of the complexes with the second molecule. Preferably, this largest number is at least fifty percent. Generally, molecules involved in a specific binding event have areas on their surfaces or in cavities giving rise to specific recognition between the molecules binding to each other. Examples of specific binding include antibody-antigen interactions, enzyme-substrate interactions, formation of duplexes or triplexes among polynucleotides and/or oligonucleotides, receptor-ligand interactions, and the like. As used herein, "contact" in reference to specificity or specific binding means two molecules are close enough that weak noncovalent chemical interactions, such as Van der Waal forces, hydrogen bonding, base-stacking interactions, ionic and hydrophobic interactions, and the like, dominate the interaction of the molecules.

"Terminator" means a nucleotide that cannot be extended by a nucleic acid polymerase. Typically, a terminator can be incorporated into a primer by a polymerase extension reaction, such that the incorporated nucleotide prevents subsequent incorporation of nucleotides to the primer and thereby halts further polymerase-mediated extension. A variety of terminators are disclosed in the following references: Chidgeavadze et al., Nucleic Acids Res., 12: 1671-1686 (1984); Chidgeavadze et al., FEBS Lett., 183: 275-278 (1985); Izuta et al, Nucleosides & Nucleotides, 15: 683-692 (1996); and Krayevsky et al, Nucleosides & Nucleotides, 7: 613-617 (1988). Nucleotide terminators also include reversible nucleotide terminators, e.g. Metzker et al. Nucleic Acids Res., 22(20):4259 (1994). "Ligatable terminators" means a terminator that has a group at its 3' position that prevents subsequent incorporation of nucleoside triphosphates, but which is capable of participating in a ligation reaction. In one aspect, a ligatable terminator has a 3' amino group.

"$T_m$," or "melting temperature," is the temperature at which a population of double-stranded nucleic acid molecules becomes half dissociated into single strands. Several equations for calculating the Tm of nucleic acids are well known in the art. As indicated by standard references a simple estimate of the Tm value may be calculated by the equation. Tm=81.5+0.41 (% G+C), when a nucleic acid is in aqueous solution at 1 M NaCl (see e.g., Anderson and Young, Quantitative Filter Hybridization, in Nucleic Acid Hybridization (1985). Other references (e.g., Allawi, H. T. & SantaLucia, J., Jr., Biochemistry 36, 10581-94 (1997)) include alternative methods of computation which take structural and environmental, as well as sequence characteristics into account for the calculation of Tm.

The above teachings are intended to illustrate the invention and do not by their details limit the scope of the claims of the invention. While preferred illustrative embodiments of the present invention are described, it will be apparent to one skilled in the art that various changes and modifications may be made therein without departing from the invention, and it is intended in the appended claims to cover all such changes and modifications that fall within the true spirit and scope of the invention.

What is claimed is:

1. A method for generating a nested set of double stranded DNA circles, the method comprising the steps of:

providing one or more double stranded DNA circles each comprising an adaptor and a DNA fragment separate from the adaptor, the adaptor containing a recognition site for a restriction endonuclease that has a cleavage site located a predetermined distance within the DNA fragment and that produces cleavage products having overhanging strands; and combining in a reaction mixture the one or more double stranded DNA circles under conditions such that the following enzymatic activities are present: (i) a restriction endonuclease activity recognizing the restriction site in the adaptor, which cleaves the DNA fragment of the double stranded DNA circles to produce linear DNA molecules having ends with overhanging strands, (ii) a polishing enzyme activity that removes overhanging strands from linear DNA molecules to produce blunt-end linear DNA molecules, and (iii) a ligase activity that forms closed double stranded DNA circles from linear blunt-end DNA molecules, whereby a cyclical reaction takes place to generate a nested set of shortened double stranded DNA circles in the reaction mixture.

2. The method of claim 1 further including the step of stopping one or more of said enzymatic activities and isolating said double stranded DNA circles.

3. A method of nucleic acid sequence analysis, the method comprising the steps of:

providing a plurality of first double stranded DNA circles, each such DNA circle having a DNA fragment and an adaptor the adaptor having at least two type IIs restriction sites oriented so that mate-pairs are produced upon cleavage with type IIs restriction endonucleases recognizing such sites and the adaptor having a third type IIs restriction site oriented so that a third type IIs restriction endonuclease recognizing such third site cleaves each double stranded DNA circle at a cleavage site proximal to the adaptor relative to that of a type IIs restriction endonuclease that produces a mate-pair;

cleaving a portion of the plurality of first double stranded DNA circles with one of the at least two type IIs restriction endonucleases and the third type IIs restriction endonuclease to produce a small linear double stranded DNA fragment and a large linear double stranded DNA fragment, each small linear DNA fragment comprising a segment adjacent to the adaptor of its first double stranded DNA circle;

circularizing the large linear DNA fragments to produce second double stranded DNA circles;

generating mate-pairs from the first and second double stranded DNA circles; and determining the nucleotide sequences of the mate-pairs adjacent to the adaptors.

4. A method for generating a nested set of double stranded DNA circles, the method comprising the steps of:

providing one or morn single stranded DNA sequences each having a primer binding site;

extending a primer annealed to the primer binding site by a nucleic acid polymerase in the presence of a ligatable terminator to form a nested set of linear double stranded DNA molecules;

treating the linear double stranded DNA molecules with a 5'-exonuclease to form blunt ends thereon; and circularizing the linear double stranded DNA molecules of the set to form a nested set of double stranded DNA circles.

5. The method of claim 4 wherein said primer has a 5'-phosphate group and wherein said step of circularization is carried out by treating said linear double stranded DNA molecules with a ligase under conditions that promote self-ligation over concatenation.

6. The method of claim 5 wherein said ligatable terminator is a 3'-aminonucleoside triphosphate.

7. The method of claim 6 wherein said one or more single stranded DNA sequences are attached to a solid support.

8. The method of claim 7 wherein said step of treating includes cleaving said linear double stranded DNA molecules from said solid support.

9. The method of claim 3 wherein said steps of cleaving and circularizing generate a nested set of double stranded DNA circles.

10. The method of claim 9 wherein said step of cleaving produces said small linear double stranded DNA fragment and said large linear double stranded DNA fragment each having ends with overhanging strands and wherein said step of circularizing includes polishing such ends to remove the overhanging strands.

* * * * *